United States Patent [19]

Rau

[11] 4,455,486

[45] Jun. 19, 1984

[54] METHOD AND APPARATUS FOR DETECTING MAGNETISM BY MEANS OF ELECTRON SPIN POLARIZATION MEASUREMENTS THROUGH DIELECTRONIC TRANSITION

[76] Inventor: Carl Rau, Feldmochingerstr. 66, Munich 50, Fed. Rep. of Germany, D-8000

[21] Appl. No.: 292,203

[22] Filed: Aug. 12, 1981

[51] Int. Cl.$^3$ .............................. G01N 23/00
[52] U.S. Cl. .................... 250/306; 250/307
[58] Field of Search .............. 250/306, 307, 251

[56] References Cited

U.S. PATENT DOCUMENTS 3,401,261  9/1968  Fuchs .................... 250/306

OTHER PUBLICATIONS

*Physics Reports (Section C of Physics Letters)*, Siegmann, vol. 17, No. 2, pp. 37–76.
"Electron–Capture Spectroscopy (ESC): A New Tool in Surface Science and Ferromagnetism", *Comments Solid State Physics*, Rau, vol. 9, No. 5, pp. 177–190 (1980).
"$1^1S$, $2^1S$, $2^3S$ States of $H^-$ and of He", *Phy. Rev.*, Pekeris, vol. 126, No. 4, pp. 1470–1476, May 1962.
"Proof that the $H^-$ Ion has only One Bound State", Hill, *Phy. Rev. Letters*, vol. 38, No. 12, pp. 643–646, Sep. 1976.
"The Colutron, A Zero Deflection Isotope Separator", Wahlin, *Nucl. Inst. And Methods*, vol. 27, pp. 55–60, Sep. 1963.
"Measurement of Surface Potential Between Ferroelectric Domains", Ferroelectrics, Bihan et al., vol. 13, No. 1–4, pp. 475–477, 1976.

*Primary Examiner*—Bruce C. Anderson
*Attorney, Agent, or Firm*—Schwartz, Jeffery, Schwaab, Mack, Blumenthal & Koch

[57] ABSTRACT

A beam of particles which undergoes a known charge state change in response to an exchange of two electrons having preoriented moments is generated. The beam is focused on a body, the magnetic properties of which are to be determined, in such a manner that the beam is reflected from the surface of the body. The number of particle charge state changes which occurred are measured in the reflected beam and provide an indication of the square of the magnetic value of the body and shows the magnetic state of the surface of the body.

10 Claims, 2 Drawing Figures

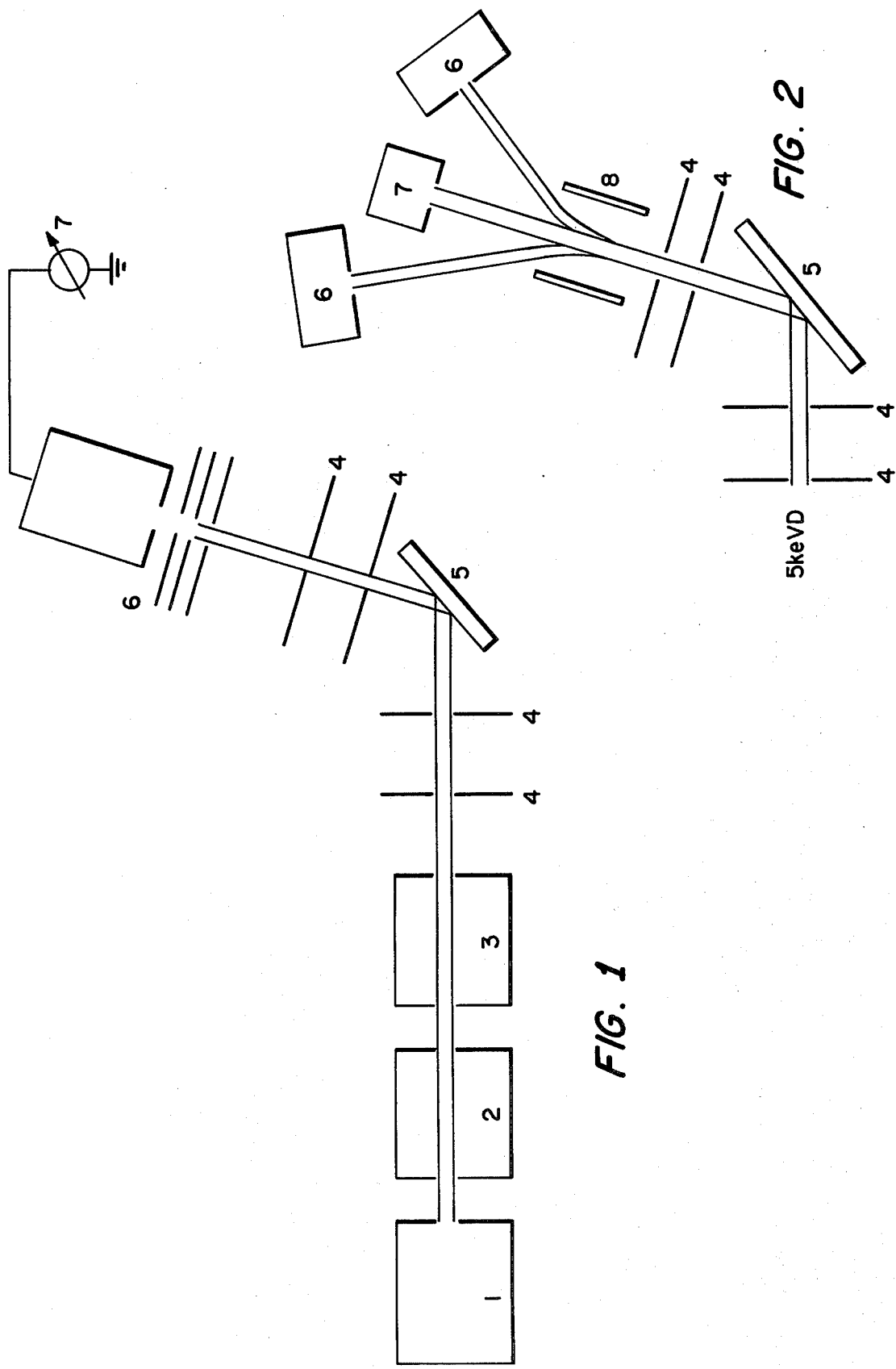

METHOD AND APPARATUS FOR DETECTING MAGNETISM BY MEANS OF ELECTRON SPIN POLARIZATION MEASUREMENTS THROUGH DIELECTRONIC TRANSITION

BACKGROUND OF THE INVENTION

1. Field of the Invention

The present invention concerns a device for the measurement of magnetic properties of surfaces of bodies, in particular ferromagnetic substances, magnetic alloys, catalysts and spin glasses.

2. Discussion of Related Art

For the measurement of magnetic properties, in most cases a magnetic field externally applied to the body is required to align the magnetic domains in a definite preferred direction, i.e., the direction of the external magnetic field. With the detector of the present invention, magnetic properties of surfaces, for example, may be detected in a very simple manner without the use of an external magnetic field.

The methods considered efficient at the present time for the investigation of magnetic properties, for example, of surfaces, employ:

(a) the emission of polarized electrons by magnetic surfaces (by field emission, photoemission) and the detection of polarized electrons accelerated to approximately 100 KeV by Mott scattering (see: H. C. Siegmann in *Phys. Rep. Phys. Lett. C* (Netherlands), Vol. 17c, No. 2, pp. 37-76 (April, 1975)); and (b) the capture of polarized electrons in ionic reflection and ion neutralization on surfaces and subsequent transfer of the electron spin polarization (ESP) by means of hyperfine interaction to produce core spin polarization, which may be used as a measurable value for the ESP (see: C. Rau in *Comments on Solid State Physics*, Vol. 9, No. 5 (1980)).

All of the methods have in common that a preferred direction in space by means of the application of an external magnetizing field is required for the alignment of the domains.

SUMMARY OF THE INVENTION

It is an object of the present invention to provide a method and apparatus for measuring magnetic properties which eliminate the need for an externally applied field and thereby also eliminate stray fields.

A further object of the present invention is to substantially simplify the existing technology for measuring magnetic properties and to provide a method for the measurement of microscopic magnetic properties on macroscopic bodies.

The above and other objects of the present invention are attained by examining the square of a magnetic value, of magnetic polarization or the ESP in the microscopic range (mm - $\mu$m), wherein ferromagnets always exhibit ferromagnetic behavior. The scattering particle beams with the exchange of two electrons, for example, by capture in the particles, is used. The lateral interaction length of the particles with the surface of a body amounts to only a few hundred atomic distances; it is always less than the lateral extension of magnetic domains. Using, e.g. small scattering angles, the particles are specularly reflected and do not penetrate into the surface of the body, a fact revealing the extreme surface sensitivity of this method. This opens a way to detect the magnetic properties of the top most surface layer of a body. This fact is highly useful to the understanding of surfaces of alloys, catalysts, spinglasses etc. The method of the invention is carried out by generating a beam of particles, which particles undergo a change of charge state by exchange of two electrons having preoriented magnetic spin moments. The beam is focused on body such that it is reflected from the surface of the body. Then the number of the particles charge state changes which occured, in the reflected beam is measured. The generation of the beam is carried out by forming the beam from H, D, He or heavier particles. The measurement may be carried out by detecting singulet and triplet states of the particles. Further, the measuring step may comprise electrostatically separating different charged components of the beam and simultaneously detecting the separated beam components and taking current measurements in the beam. Furthermore, the method may include the step of calibrating the measured number of charge state changes through the measurements of the temperature dependence of the magnetic value.

The apparatus for carrying out the present invention comprises means for generating a beam of particles, which particles undergo a known charge state change in response to an exchange of two electrons having preoriented magnetic moments; means for focusing the beam on a body such that the beam is reflected from the surface of the body; and means for measuring the number of particle charge state changes which occurred in said reflected beam.

BRIEF DESCRIPTION OF THE DRAWINGS

The above objects and advantages will become more readily apparent as the invention becomes more completely explained in the Detailed Description, reference being had to the accompanying drawings in which like numerals represent like parts throughout and in which:

FIG. 1 is a schematic drawing of one embodiment of an apparatus for carrying out the present invention; and FIG. 2 is a schematic drawing of a second embodiment of an apparatus for carrying out the present invention.

DETAILED DESCRIPTION OF THE PREFERRED EMBODIMENTS

In dielectronic exchange in the atomic shell of a particle in scattering there are two boundary cases:

In the interchange of two electrons with magnetic moments antiparallel to each other, at a body to be examined, a *singulet* state would be produced in the particle (for example $H^+ + 2\ e = H^- (1s^2)$). In the other case of the transition of two electrons with magnetic moments parallel to each other, a triplet state would be generated ($H^+ + 2\ e = H^- (1s2s)$).

A very simple path to a solution results from the use of hydrogen particle beams. It is known that $H^-$ ($1s^2$) exists in the singulet state, but not in the triplet state ($H^-$ ($1s2s$)). References: C. L. Pekeris, *Phys. Rev.*, Vol. 126, pp. 1470-1476 (Jan., 1962) and R. Hill, *Phys. Rev. Lett.*, Vol. 38, pp. 643-646 (Sept., 1976). This signifies in the present case that the measurement of the magnetic value may be reduced to a simple measurement of the state of charge, i.e., to current measurements. This may be effected, following the electrostatic separation of the charges ($H^+$ component and $H^-$ component of the current) by means of Faraday cups or electrostatic energy and angle analyzers.

A high ESP value (numerous parallel moments of electrons) thus signifies the formation of few $H^-$. A low ESP (numerous antiparallel moments available for interchange) then means the formation of more $H^-$ than with a high ESP value.

Example: A paramagnet such as Copper has zero ESP; the $H^-/H^+$ ratio is then larger than in the scattering of particles on a surface of a ferromagnetic body such as Ni.

The use of hydrogen particles, since only the singulet state exists, is extremely simple for the execution of the measurement. A further possibility naturally consists using heavier particles, such as He, etc. The effective cross section for the neutralization, exchange and capture rates of electrons always depends on the size of the particles. The latter differs for example for singulet and triplet helium (Pauli exclusion principle). Obviously, this provides in principle a sensitivity for the measurement of a magnetic value. Example: the neutralization of $He^{++}$ to $He^O$ by means of dielectronic capture on the surface of the magnetic body. The $He^O/He^{++}$ neutralization rate naturally depends on the magnetic properties of the body.

In an investigation of excited particles and in measurements of light emission, these values may also be measured.

The advantages to be attained by the invention include the fact that in place of a complex apparatus with magnetic fields applied to the specimens, it is now possible to effect investigations without the application of fields, simply and inexpensively, using nonprofessional personnel. The testing of a body to determine whether it is magnetic or not (specifically its uppermost atomic layer) may now be effected by means of simple current measurements.

With reference to FIGS. 1 and 2, the apparatus to be used will now be set forth. A HF ion source 1 with a Wien filter 3 (ortec Model 320 and a velocity filter according to L. Wahlin, *Nuclear Instr. Meth.*, Vol. 27, pp. 55–60 (Sept., 1963)) produces energetic ions (D+) in an energy range of up to 10 KeV (high rate of $H^-$ or $D^-$ formation in this energy range) with a high intensity through a small solid angle (approximately 0.5°). A magnetic body 5 with a smooth surface produces the small angle scattering of approximately 5 KeV D+ ions at an angle of approximately 1° against the surface. Measurement of the reflected particles is made by a Faraday cup 6 with bias voltages for the separate measurements of the $D^-$ and $D^+$ components in the beam reflected at an angle around 1° by the surface. The measurements are effected in a vacuum.

EXPLANATION OF FIG. 1

A beam generator 1 generates a beam of particles which is passed through electrostatical lenses 2 and subsequently through a Wien filter 3 to allow only single charged positive ions or if wanted doubly charged positive ions to leave and to reach apertures 4 (diaphragms, beam collimators) to strike a surface of a body 5. After reflection at the surface of the body the beam passes apertures 4 and then hits a Faraday cup 6 which is biased to detect either positive or negative particles. The ion current is measured with a current meter 7.

The beam generator 1 is a commercial ion source of type Model 320 RF Ion source from Ortec Inc. or Ionex. Inc. or is a Colutron Ion source from Colutron. These beam generators provide particle beam accelerated to 500 Volts up to 30,000 Volts.

The lenses 2 are standard electrostatical focussing devices and consist of stainless steel tubes at high voltage.

The Wien filter 3 is a velocity filter for particle beams and consists of crossed electric and magnetic fields to separate and to disperse parts of a beam in such a way that only one velocity selected part of the beam is striking pairs of diaphragms used for collimating the beam.

The beam diaphragms 4 consist of stainless steel plates with a hole for beam passage and collimation.

The magnetic body 5 is mounted on a target holder and consists of any magnetic material to be investigated. In case of calibration, this magnetic body can be replaced by a nonmagnetic body by lateral movement of the target holder.

After reflection, the beam passes pairs of diaphragms 4 for defining a fixed solid angle in space.

A Faraday cup 6 is a standard equipment to measure current. Dependent on the bias voltage positive or negative current can be collected.

The electrical current itself is measured using a standard Ampere meter 7.

Calibration of the charge states in the reflected beam is performed by monitoring the beam current at the magnetic body 5.

EXPLANATION OF FIG. 2

Deuterium gas is ionized in a RFion source and accelerated to 5 KeV by a voltage. After the focusing and selecting the D+-part of the beam by using the Wien filter a 5 KeV D+ beam strikes a magnetic body. Before reflection, the beam is collimated using stainless steel apertures which generate a beam of divergence of less than 0.1 degree.

During the reflection at the magnetic body part of the beam effects electron exchange with the magnetic body.

After reflection, the beam passes apertures (diaphragms) and then passes an electrostatical condensor to separate charged and neutral parts of the beam. 6 are detectors for positive or negative charged beams, e.g., Faraday cups. 7 is a detectors for neutral particles, e.g., there the neutral particles are again ionized and the electrical currents are measured.

The above description is set forth for purposes of illustration only, it being understood that numerous changes, modifications and additions may be made to the present invention without departing from the scope thereof as set forth in the appended claims.

What is claimed is:

1. A method for determining the magnetic characteristics of a body, comprising:
   generating a beam of particles, which particles undergo a known charge state change in response to an exchange of 2 electrons having predetermined magnetic moments;
   focusing said beam on said body such that said beam is reflected from the surface of said body; and
   measuring the number of particle charge state changes which occurred as a result of an exchange of 2 electrons in said reflected beam, as an indication of the magnetic value of the body.

2. The method as set forth in claim 1, wherein the step of generating a beam comprises forming said beam from He and heavier particles.

3. The method as set forth in claim 2, wherein the step of measuring comprises detection of singulet and triplet states of said particles.

4. The method as set forth in claim 1, wherein the step of measuring comprises electrostatically separating different charged components of said beam and simultaneously detecting the separated beam components.

5. The method as set forth in claim 1, wherein the step of measuring comprises taking current measurements in said beam.

6. The method as set forth in claim 1 and further including the step of calibrating the measured number of ionization state changes through measurements of the temperature dependence of the magnetic value.

7. Apparatus for determining the magnetic characteristics of a body, comprising:
   means for generating a beam of particles, which particles undergo a known ionization state change in response to an exchange of two electrons having predetermined angular moments;
   means for focusing said beam on said body such that said beam is reflected from the subface of said body; and
   means for measuring the number of particle ionization state changes which occurred as a result of an exchange of 2 electrons in said reflected beam, as an indication of the magnetic value of the body.

8. The apparatus as set forth in claim 7, wherein said particles comprise H, D, He or heavier particles.

9. The apparatus as set forth in claim 8, wherein said means for measuring includes means for detecting singulet or triplet states of said particles.

10. The apparatus as set forth in claim 7, wherein said means for measuring comprises electrostatically separating differing charged components of said beam.

* * * * *